United States Patent [19]

Tarnowski et al.

[11] Patent Number: 5,026,905

[45] Date of Patent: Jun. 25, 1991

[54] FLUORESCENT DYES

[75] Inventors: Thomas L. Tarnowski, South San Francisco; Mae W. Hu, Los Altos Hills; Maureen Laney, Palo Alto; John S. Pease, Los Altos; Vartan Ghazarossian, Menlo Park, all of Calif.

[73] Assignee: Syntex (U.S.A.) Inc., Palo Alto, Calif.

[21] Appl. No.: 234,361

[22] Filed: Aug. 19, 1988

Related U.S. Application Data

[63] Continuation-in-part of Ser. No. 645,458, Aug. 28, 1984, Pat. No. 4,748,129.

[51] Int. Cl.$^5$ .................... C07C 229/18; C07F 9/09
[52] U.S. Cl. .......................... 562/43; 558/48; 558/176; 562/11; 562/16; 562/37; 562/440
[58] Field of Search ............... 558/48, 176; 562/11, 562/16, 37, 43, 440

[56] References Cited

U.S. PATENT DOCUMENTS

| | | | |
|---|---|---|---|
| 4,500,621 | 2/1985 | Wurster | 430/72 |
| 4,508,803 | 4/1985 | Law et al. | 430/59 |
| 4,564,598 | 1/1986 | Briggs | 436/501 |
| 4,707,427 | 11/1987 | Tanaka et al. | 430/59 |
| 4,751,327 | 6/1988 | Kazmaier et al. | 564/307 |

OTHER PUBLICATIONS

Liebesking et al., "Journal Org. Chem.", 53:2482-88, (1988).
Springer et al., "Ang. Chem. Intl. Edit.", vol. 7:530, (1968).
Kim et al., "J. Chem. Soc., Chem. Commun.", :1201, (1987).
Sprenger et al., "Angew. Chem. Intl. Edit.", vol. 5:894, (1966).

*Primary Examiner*—Richard L. Raymond
*Attorney, Agent, or Firm*—Theodore J. Leitereg; Linda J. Nyari

[57] ABSTRACT

The present invention describes a class of dyes for use in staining cell samples and methods of making such dyes. A preferred class of dyes known as detergent dyes which possess the ability to stain cells in whole blood and are only slowly leached or lost from the stained cells over time are described. The present invention has application, for example, to blood typing for the determination of the presence of blood group antigens A, B, AB, O, and D ($Rh_o$) and antibodies to such antigens.

4 Claims, No Drawings

FLUORESCENT DYES

This is a continuation-in-part of copending application U.S. Ser. No. 645,458 filed Aug. 28, 1984, now U.S. Pat. No. 4,748,129, incorporated herein by reference.

BACKGROUND OF THE INVENTION

Field of the Invention

There is a continuing need for improved assay methods and reagents for the detection of an analyte in a sample. The analyte can be a member of a specific binding pair ("sbp") consisting of ligand and its homologous receptor. Exemplary of sbp members are antigens and antibodies.

In general, a sbp member complementary to the antigen will be used as an assay reagent. Other reagents used in detection assays must have particular characteristics in order to be suitable for use in the assay. When the analyte is on the surface of a particle or can be caused to bind to a particle, it is desirable to use a dye, for example a fluorescent dye, capable of staining the particle in a reproducible manner without interfering with the reaction between the analyte and its homologous sbp member.

Mammalian red blood cells carry numerous antigens some of which must be accurately identified in both patient and donor for medical procedures such as transfusions. Accurate determination of blood groups, A, B, AB, O and D ($Rh_o$) is critically important. Also, antibodies to such blood group antigens as well as other circulating antigens can be of diagnostic interest.

Conventionally, agglutination techniques are performed on a microscope slide or in a tube with the results being assessed visually. Improved rapid, accurate and automated screening of blood is desirable in view of the critical nature of the assays performed, the labor intensity of such assays and the large numbers of samples which must be tested.

BACKGROUND OF THE INVENTION

Researchers in the field have used such terms as squarate, squaraine and squarylium to describe the various compounds which have as their root squaric acid.

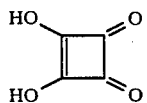

For purposes of this invention, reference to the works of others will use the terminology as used in the particular reference. In describing the instant invention, the term "squaraine" will be used when referring to the squaraine compound which is derived from squaric acid and modified so as to possess the desired fluorescent dye properties.

Various squaric acid dyes are discussed by Sprenger, et al., *Angew. Chem.*, 80, 541 (1968); Sprenger, et al., *Angew. Chem.*, 79; 581, 1967; Sprenger, et al., *Angew. Chem. internat. Edit.*, 5:894 (1966); and Maaks, et al., ibid., 5:888 (1966).

Novel squaraine dyes having absorption maximums of greater than 600 nm and possessing either hydrophilic or lipophilic properties are described in the pending U.S. application, Ser. No. 834,168 filed Feb. 27, 1986.

Assays for ligands and receptors employing the novel squaraine dyes are described in pending U.S. application, Ser. No. 773,401 filed Sept. 6, 1985. Use of fluorescent beads conjugated to a receptor for the screening of red blood cells is described in U.S. Pat. No. 4,550,017 issued Oct. 29, 1985.

Identification of red blood cell antigens by agglutination techniques is standard, e.g., C. Hudson and F. C. Hay, *Practical Immunology*, Second Edition, Blackwell Scientific Publications, Oxford (1980). U.S. Pat. No. 3,862,303 is exemplary of immunological detection and identification of serological factors using carrier particles such as latex beads. Smith, FEBS Letters 77,25 (1977) describes a fluorescent immunoassay.

More recently squaric acid compounds for use in the preparation of electrophotographic plates of use in electrophotographic imaging systems have been described. In particular, squaric acid dyes having photoconducting abilities are described in U.S. Pat. No. 4,500,621 issued Feb. 19, 1985. Use of more squaraine compositions in photoresponsive devices having sensitivity to infrared and visible illumination is described in U.S. Pat. No. 4,508,803 issued Apr. 2, 1985. In particular, fluorobenzylamino derivatives of squaric acid are described.

In yet another use of squaric acid compounds in electrophotography, squarylium compounds having straight chain alkyl groups with a hydroxyl or halogen atom attached are described in U.S. Pat. No. 4,707,427 issued Nov. 11, 1987.

SUMMARY OF THE INVENTION

Fluorescent agents are provided for determining the presence in a sample of a member of a specific binding pair ("sbp member") consisting of ligand and its homologous receptor. The fluorescent agents are squaraine dyes which can readily be absorbed by cells in whole blood or in suspension in other aqueous media. In one embodiment of the invention, the squaraine dye is from the class of squaric acid dyes referred to herein as detergent dyes. The dye is so designed as to enter the cell in the presence of proteins and other plasma components and to be retained by the cell. Leaching out of the dye occurs slowly if at all.

The squaraine dye of the invention is a compound of the formula:

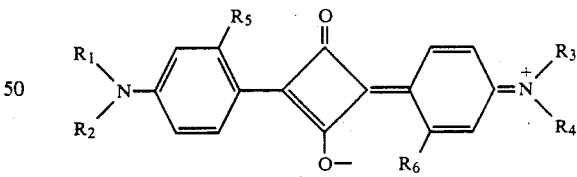

wherein:

$R_1$ and $R_2$ are independently selected from the group consisting of lower alkyl (1-5 carbon atoms) with the proviso that at least one of the $R_1$ and $R_2$ groups has a substituent selected from the group consisting of —$SO_3H$, —$OSO_3H$, —$PO_3H_2$, —$OPO_3H_2$, —COOH and —$NHSO_3H$;

$R_3$ and $R_4$ are independently selected from the group consisting of alkyl (5-15 carbon atoms); and $R_5$ and $R_6$ are independently selected from the group consisting of hydrogen, hydroxyl, and lower alkoxyl (1-5 carbon atoms).

In the method, the sample believed to contain an sbp member is combined in an aqueous medium with a complementary sbp member wherein at least the sbp member or the complementary sbp member is bound to the surface of a cell. The cell is stained with a fluorescent agent, i.e. the squarine dye, capable of being incorporated into the cell. The presence of the sbp member is indicated by a change in fluorescence of the cell suspension as a result of agglutination of the cells.

The present invention has particular application to blood typing, for example, for the determination of the presence of blood group antigens A, B, AB, O, and D ($Rh_o$) and antibodies to such antigens, as well as antibodies to antigens M, N, S, s, Lewis, Lutheran, Kell, Duffy, Kidd, etc.

DESCRIPTION OF THE SPECIFIC EMBODIMENTS

The subject invention provides novel reagents and methods of making such reagents for determining the presence of an analyte, usually a sbp member, in a sample. The method of detection employs a complementary sbp member where at least one of either the sbp member or the complementary sbp member is bound to the surface of a cell. Also employed in the method is a fluorescent cell incorporative agent.

Preferably, when the sbp member in the sample is not bound to the surface of a cell and the sample contains cells, the fluorescent agent is combined with the sample by first incorporating the agent into cells bound to a complementary sbp member and then combining the combination with the sample. When the sample does not contain cells, the dye can be added before or after combining the sample with cells, or by combining the sample with stained cells. When the sbp member in the sample is bound to the surface of a cell, the fluorescent agent can be added to the sample either prior to or after combining the sample with the complementary sbp member. Preferably, the fluorescent agent is added to the sample prior to combining the sample with the complementary sbp member. Thus, the term "combining with the sample" is meant to include combining together two or more of the reagents mentioned above prior to combining any remaining reagents. The term "reagents" includes the sample, the complementary sbp member (bound or not bound to the cells), and the fluorescent cell incorporative agent, and may further include any additional agents required for the successful operation of the subject method.

Before proceeding further a number of terms will be defined.

"Fluorescent cell incorporative agent"—a compound of molecular weight less than 2000 capable of being incorporated into a cell and thereby causing the cell to be fluorescent, for example, a cell membrane soluble dye, a DNA intercalating dye, a vital dye or the like.

"Sbp member"—a member of a specific binding pair consisting of two different molecules, where one of the molecules has an area on the surface or in a cavity which specifically binds to a particular spatial and polar organization of the other molecule. The two members of a specific binding pair are referred to as ligand and receptor (antiligand) and are also referred to as complementary or homologous.

"Ligand"—any organic compound for which a receptor naturally exists or can be prepared;

"Receptor" (antiligand)—any macromolecular compound or composition capable of recognizing (having an enhanced binding affinity to) a particular spatial and polar organization of a molecule, i.e., epitopic or determinant site. Illustrative receptors include naturally occurring receptors, e.g., thyroxine binding globulin, antibodies, enzymes, Fab fragments, lectins, and the like. The term antibody is employed in this case as illustrative of, and to more generally denote, receptor.

"Analyte"—the compound or composition to be measured, which is a sbp member and may be a ligand, which is mono- or polyvalent, that is, having one or a plurality of determinant sites, haptenic and antigenic, a single compound or plurality of compounds which share at least one common epitopic or determinant site; or a receptor.

"Complementary sbp member"—the homologous member of a specific binding pair where the sbp member is an analyte.

"Cell"—any one of the minute protoplasmic masses which make up organized tissue, comprising a mass of protoplasm surrounded by a membrane including nucleated and unnucleated cells and organelles.

The fluorescent cell incorporative agent is preferably more fluorescent after incorporation into a cell. It may be capable of incorporation into the cell by virtue of being soluble in the cell membrane or of being transportable across the cell membrane and undergoing a chemical reaction that inhibits transport out of the cell. Fluorescent agents with high protein or carbohydrate affinity may also be useful in the present invention. Where the cells possess deoxyribonucleic acid (DNA), one may also employ fluorescent agents having an affinity for DNA. The fluorescent cell incorporative agent may be a hydrophobic dye that can be rendered water soluble by binding to a hydrophilic carrier.

The fluorescent cell incorporative agent should preferably have an absorption maximum greater than 450 nm, more preferably greater than 540 nm, to provide maximum avoidance of biological interference. For the most part, the absorption wavelength maximum should be 320 to 1000 nm, preferably 600 to 800 nm.

The molar extinction coefficient for the fluorescent cell incorporative agent at the wavelength of the exciting light should be as high as practical and should be greater than 1,000, preferably greater than 10,000, most preferably greater than 100,000 liter mole$^{-1}$ centimeter$^{-1}$. Fluorescent cell incorporative agents are chosen to have a high quantum yield, normally greater than 0.05, preferably greater than 0.3 when incorporated in cells. The excitation wavelength is chosen to minimize background fluorescence from the sample, maximize fluorescence of the stained cells, and maximize the intensity of the light source and reliability of the filters. Particularly advantageous wavelengths are 490 nm and 525 nm, and 633 nm because of the availability of these wave lengths from Argon, and Helium/Neon (He/Ne) lasers, respectively. In general, longer wavelengths minimize background. A He/Ne laser tuned to 633 nm is particularly desirable and dyes with a high quantum yield and a high molar coefficient of extinction at 633 nm are therefore preferred.

In addition, it is desirable that the fluorescent cell incorporative agent have an emission maximum at a wavelength that is preferably at least 15 nm, more preferably at least 30 nm longer than the excitation wavelength to be used. In general, it is preferred that there be a substantial spread or difference in wavelengths for such fluorescent agent between its absorption maximum and emission maximum.

The fluorescent agent should remain substantially incorporated in the cell during the time of the assay, particularly where cells containing such fluorescent agent are to be mixed with a sample containing other cells. Furthermore, it is preferable that the fluorescent cell incorporative agent not be substantially quenched when incorporated into a cell relative to when it is in an aqueous environment. That is, the product of the extinction coefficient and the quantum yield at a given excitation wavelength should not be greatly reduced when the fluorescent agent is incorporated in the cell relative to when the fluorescent agent is not incorporated in the cell. Although an increase in fluorescence is not required, it is usually preferable that the fluorescence of the cell incorporated agent when in the cell be at least one third, preferably at least equal to that of the unincorporated fluorescent agent.

A further characteristic of the fluorescent cell incorporative agent is that it not interfere with binding of the sbp members, e.g., binding of the antigen and antibody. The fluorescent cell incorporative agent should preferably also exhibit a high affinity for the cell.

The number of fluorescent cell incorporative agent molecules per cell should be sufficient to conduct a meaningful assay, generally being about $10^2$ to $10^7$ of such molecules per cell, preferably $10^3$ to $10^6$ of such molecules per cell.

As mentioned above, a preferred class of fluorescent cell incorporative agents comprises fluorescent dyes that are soluble in the cell membrane, which means that the dyes are hydrophobic and will usually be amphiphilic to provide for sufficient water solubility to permit the agent to be incorporated in the cells in a reasonable time when added to an aqueous suspension of the cells. A preferred group of membrane soluble dyes includes certain squaraine dyes that have an absorption maximum greater than 600 nm and an appropriate molar extinction coefficient and Stokes' shift.

A preferred class of fluorescent cell incorporative agents comprise dyes that will stain cells in substantially undiluted whole blood; that is, blood that is less than two fold diluted. A particularly preferred subclass of these dyes are not released from the cells to a significant extent during the course of an assay in which the cells are diluted or resuspended in a different medium. Thus, on incubation with neat plasma the fluorescence of the stained cells will decrease by less than 30% in 10 minutes, preferably less than 20% in 20 minutes, most preferably, less than 10% in 30 minutes.

Exemplary of such dyes by way of illustration and not limitation are those of the formula:

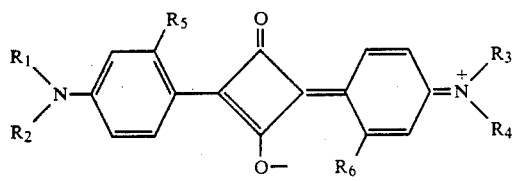

wherein $R_1$ and $R_2$ may be unsubstituted and independently selected from the group consisting of lower alkyl (1-5 carbon atoms) or substituted with one or more substituents selected from the group $-SO_3H$, $-COOH$, $-PO_3H_2$, $-OSO_3H$, $OPO_3H_2$ and salts thereof; and $R_3$ and $R_4$ are each independently selected from the group consisting of alkyl of from 5 to 15 carbon atoms; and $R_5$ and $R_6$ are independently selected from the group consisting of hydrogen, hydroxyl and lower alkoxyl (1-5 carbon atoms).

Squaric acid dyes wherein the substituents on the R-groups are lower alkyl groups are disclosed by Sprenger, et al., *Angew. Chem. Internat. Edit.*, 5:894, 1966.

A class of squaric acid dyes of the general formula described above where $R_1$ is substituted with one or more substituents selected from the group $-SO_3H$, $-COOH$, $-PO_3H_2$, $-OSO_3H$, $OPO_3H_2$ or salts thereof are called "detergent dyes". This class of squaraine compounds is preferably prepared by coupling of squaric acid to two groups of very different hydrophilicity. These detergent dyes contain groups that can ionize to form a cation or anion, preferably an anion, most preferably a sulfonic acid, and have absorbance maxima above 600 nm with high extinction coefficients and high fluorescence quantum yields.

The detergent dyes are conveniently synthesized in the presence of a polar aprotic solvent and a conventional solvent. Conventional solvents include lower alcohol:aromatic solvent mixtures, for example, n-butanol:benzene, n-butanol:toluene and the like. Preferably, included with the alcohol:aromatic solvent mixture are diols, such as ethylene glycol or propylene glycol or suitable polar aprotic solvent, for example, dimethylsulfoxide (DMSO), dimethyl formamide (DMF), dimethylacetamide, dimethyl sulfone, sulfolane, and hexamethylphosphoric triamide. More preferably, DMSO or ethylene glycol is used as a cosolvent in the reaction mixture. Use of DMSO results in the efficient coupling of squaric acid with two groups possessing very different hydrophilicity. In one of the preferred synthesis reactions, DMSO is used to produce a squaraine dye of the formula given above wherein $R_3$ and $R_4$ are hydrocarbon chains and $R_1$ and/or $R_2$ are further substituted with a sulfonic acid. Detergent dyes having unsubstituted hydrocarbon chains of from 5 to 8 carbons are preferred.

While the detergent dyes can be prepared using standard conditions, i.e., refluxing n-butanol-benzene or n-butanol-toluene, the addition of a polar aprotic solvent, such as DMSO, in the synthesis has been shown to greatly enhance the efficiency of coupling with the squaric acid. Addition of from 5-30% (vol.:vol.) of DMSO, preferably 10-20%, has been shown to enhance the synthesis of the detergent dye. Illustrative descriptions of the synthesis and purification of the detergent dyes are set forth in Examples 2, 3 and 4.

Desirably, a dye for use in the assay of this invention must fulfill the following requirements: an absorbance preferably greater than 600 nm; an extinction coefficient of at least 150,000 liter mole$^{-1}$ centimeter$^{-1}$; a fluorescent quantum yield of at least 0.1; the ability to stain cells to provide a source of fluorescence; no interference with the antigens of interest; and, the ability to remain in the cell during the assay. As a class, the detergent dyes meet these requirements exceptionally well.

In carrying out one embodiment of the present method, the sample, a sbp member complementary to the analyte, and the fluorescent cell incorporative agent are combined in an aqueous assay medium and a change in fluorescence of the mixture as a result of agglutination of the cells is then determined. The presence of the analyte in the sample is indicated by this change in fluorescence.

The present method is adaptable to a wide variety of assay determinations for a wide variety of sbp member analytes. It is of special interest where at least one of the analyte and its complementary sbp member is a normal component of the cell surface. Cell surface sbp members include naturally occurring membrane components such as antigens, cell wall antigens, particularly bacterial cell walls, cell surface receptors including receptors for activating, growth, and inhibition factors, antibodies, HLA antigens, Fc receptors, hormone receptors, ion channels, glycolipids, lipoproteins, complement components, viral antigens, membrane bound enzymes, peptidoglycan, fungal antigens, idiotypic antigens and the like. Cell types of interest include leukocytes, bacteria, fungal cells, erythrocytes, gametocytes, reticulocytes, lymphocytes including monocytes, macrophage, B cells, T cells, eosinophils, etc. A particular adaptation of the present method is in the area of blood typing. Blood group antigens, as well as antibodies thereto, may be detected using the method described above.

The subject invention provides a novel and particularly useful method for typing red blood cells or identifying red blood cell antigens and the antibodies thereto by using the red blood cells as a carrier of incorporated fluorescence where the cells agglutinate during the assay method. A change in fluorescence as a result of the agglutination is determined and is an indication of the presence of a particular red blood cell antigen or antibody thereto. Substances which bind to red blood cell antigens, normally antibodies or lectins, are required to cause agglutination of the cells. In one embodiment of the present invention for determining blood group antigens, whole blood is combined with a fluorescent cell incorporative agent, usually a squaraine compound of the above formula where $R_3$ and $R_4$ are unsubstituted, and preferably $R_1$-$R_4$ are ethyl, and a receptor for the antigen of interest in an aqueous medium, e.g., an appropriate buffer. If the antigen of interest is present on the surface of the red blood cells agglutination of the cells will occur and a change in fluorescence will be observed as an indication of the presence of the antigen of interest.

The receptor which is employed binds preferentially to the blood group surface antigens of interest. Thus, there will be a fluorometrically measurable change when a given antigen is present as compared to when that antigen is absent in a given red blood cell sample. For example, in the A, B, O system, if anti-A antibody were used, agglutination would occur and there would be a change in fluorescence if the analyte contained the A antigen of type A or type AB blood over that where the analyte contained blood types B or O.

In addition to antibodies, certain lectins are known to bind specifically to red blood cell surface antigens, and are convenient receptors for use in the present assays.

The compounds and methods described herein can also be used for determining the presence of antibodies to a red blood cell antigen. In this approach, red blood cells having the surface antigen homologous to the antibody in question are employed in the assay. The antigen-bearing cells and a fluorescent agent are preferably combined first to provide stained cells which are then combined with the sample in an aqueous medium. Staining will frequently be achieved with a detergent dye of the invention, preferably where $R_3$ and $R_4$ are octyl or heptyl, $R_1$ is ethyl and $R_2$ is trimethylene sulfonic acid. Alternatively, a squaraine dye of the invention, where $R_1$-$R_4$ are independently selected from the group butyl, pentyl and hexyl can be used for antibody screening assays. If the antibody in question is present in the sample, a change in fluorescence will occur as the result of agglutination.

The present method is of particular importance in cross-match determinations. In such a determination, blood cells from a potential donor and plasma from a recipient are mixed in accordance with the method of the invention. Preferably, whole blood from the donor will first be combined with the fluorescent agent in order to stain the cells and the mixture will then be combined with recipient plasma. Alternatively, the fluorescent agent may be added after combining the blood and plasma. After incubation, the cells are separated, washed, and suspended and incubated in a solution that contains anti-immunoglobulin. A positive signal caused by agglutination indicates that the match is incompatible. The successful use of this method requires the fluorescent agent be a detergent dye. Most preferably, the detergent dye is of the general formula described above where $R_3$ and $R_4$ are octyl or heptyl, $R_1$ is ethyl and $R_2$ is trimethylene sulfonic acid.

The method described herein is simple and can be performed in a reasonably short period of time. A particular advantage of the present method is that cells in whole blood can be stained directly with no prior separation or washing of donor cells. Cells stained by this method retain the fluorescent dye during the subsequent washing, suspending, and separation steps. The assay medium or mixture may, therefore, be observed directly for a change in fluorescence as a result of agglutination of the cells.

A method utilizing the dyes of the invention will next be described in detail using a blood sample as exemplary of the assay sample and blood group antigens, or antibodies thereto, as exemplary of sbp members that may be determined in accordance with the present method. This description is by way of illustration only and is not meant to limit the scope of the present invention.

In one procedure for carrying out an assay for a blood group antigen which is a sbp member in accordance with the present invention, a blood sample optionally in a buffered aqueous medium comprising greater than 5%, preferably greater than 20%, more preferably greater than 50%, blood by volume is employed. The pH of the buffered aqueous medium is usually about 5 to 9, preferably about 6 to 8. The sample is mixed with appropriate amounts of a fluorescent cell incorporative agent and a sbp member complementary to the blood group antigen, which amounts generally should be sufficient to result in a meaningful assay. The amount of the fluorescent cell incorporative agent depends upon the nature of the cells and the nature of the agent. Usually, about 0.1 to 100 µg, preferably about 1 to 10 µg, of fluorescent cell incorporative agent are employed per ml of blood. The amount of complementary sbp member employed is determined empirically and is usually between 0.01 and 1000 or more times the amount of blood group antigen, preferably 0.1 to 100 times the amount of blood group antigen.

Where the fluorescent cell incorporative agent has low water solubility, a solution of the fluorescent agent in a suitable organic polar solvent will be added to the blood sample. Normally the volume of the added solution will be 5% less of that amount of the blood sample, preferably 3% or less. The organic solvent will generally have from 1 to 6 carbon atoms and from 1 to 5 heteroatoms selected from the group consisting of oxygen, nitrogen, and sulfur. Exemplary of such solvents are dimethylformamide, dimethylsulfoxide, hexamethylphosphoramide, and the like. The mixture is then combined with the complementary sbp member.

The sample, fluorescent cell incorporative agent, and complementary sbp member are combined and incubated under conditions, usually mixing, that will provide for agglutination of the cells when the blood group antigen of interest is present. Incubation times may vary widely depending on the density of the blood group antigen on the cell surface, the concentration of the cells and the complementary sbp member and the reaction conditions including the addition of agglutination enhancers such as polybrene, dextran or dextran derivatives, low ionic strength medium, serum albumin, polyethyleneglycol, and the like. Desirable incubation times are about 10 to 600 sec, preferably about 10 to 200 sec, at mild temperatures usually about 10° to 37° C.

In reverse blood grouping for the determination of the presence of antibodies to a particular blood group antigen in a sample, a sample of plasma or whole blood is combined in an aqueous buffered medium with red blood cells of the particular type, A or B, of interest. The fluorescent cell incorporative agent is incorporated into such cells prior to combining with the sample when the sample is whole blood, but can be added after combining the sample with the cells when the sample is plasma. Incorporation of such agent into the red blood sample is carried out as described above. The medium is then held for a period and under conditions for agglutination as mentioned above.

Following the above holding period, the medium is examined to determine any change in fluorescence as a result of agglutination of the cells.

Changes in fluorescence may be measured in various ways. In one procedure, agglutination produces a decrease in fluorescence because a cellular component such as hemoglobin absorbs more incident or emitted light from a cell in a cell cluster than from a cell that is unassociated with other cells. Other methods depend upon the distribution of fluorescent molecules as a result of aggregation.

To this end one may use a non-flow cytometric technique known in the art, in which a small diameter beam of light produced by means of slits or preferably a laser is used to detect high local concentration of fluorescent molecules. This technique employs fluorescent pulse height analysis or correlation of fluorescence fluctuations: Briggs, et al., "Homogeneous Fluorescent Immunoassay," *Science*, 212:1266 (1981) and Nicoli, et al., "Fluorescence Immunoassay Based on Long Time Correlations of Number Fluctuations," *Proc. Natl. Acad. Sci. USA*, 77(8):4904 (1980).

A preferred method for determining a change of fluorescence in accordance with the present invention involves the use of the fiber optic cytometer described in U.S. Pat. No. 4,564,598 issued Jan. 14, 1986 and having the same assignee as the present invention, the disclosure of which is incorporated herein in its entirety. In U.S. Pat. No. 4,564,598, method and apparatus are provided for determining the presence of particles in a dispersion in relation to the detection of the presence or amount of the material of interest. An optical fiber is used to define a relatively small volume from which fluorescent light can be received and counted. The volume is related to the volume in which there is likely to be one or relatively few particles which produce predetermined fluctuations. By employing any one of several mathematical techniques for fluctuation analysis, the fluorescence fluctuations are related to the presence of an analyte in a sample. The fluctuations are observed over a period of time in a static mode or preferably by sampling a plurality of volumes in the sample. By comparing the observed results with results obtained with samples or calibrators known to be free of analyte and other samples or calibrators known to contain the analyte, the presence or absence of analyte in unknown samples can be determined.

As a calibrator blood grouping, a known amount of antibody or cells bearing the appropriate blood group antigen in question is incorporated into an appropriate medium and treated as described above for the sample containing the unknown analyte. The change in fluorescence for the calibrator is compared with the change in fluorescence for the unknown sample as an indicator of the presence of the blood group antigen or antibody thereto in question.

The fluorescent dyes of the invention can be provided in a kit in packaged combination with predetermined amounts of reagents for use in the detection of serum antigens. A representative kit would include the fluorescent dye and an sbp member complementary to the analyte. Alternatively, the kit could contain cells having a complimentary sbp on their surface which are stained with the fluorescent dye. In addition, other reagents necessary to detect the sbp member of interest in the sample and additives such as ancillary reagents may be included. The relative amounts of the various reagents may vary widely, to provide for concentrations in solution of the reagents which substantially optimize the sensitivity of the assay. The reagents will usually be provided as liquid suspensions of particles but when no cells are included they can be provided as dry powders, usually lyophilized, including excipients, which on dissolution will provide for a reagent solution having the appropriate concentrations for performing the assay.

EXAMPLES

The examples which follow are illustrative and are not limiting of the invention.

EXAMPLE 1

Preparation of
2-(p-diethylamino-m-hydroxyphenyl)-4-(diethylimmonio-2-hydroxyl-2,5-cyclohexadienylidene)-3-oxo-1-cyclobutenolate (DEAS)

DEAS was prepared as follows: squaric acid (741 mg, 65 mmole) was mixed with stirring with 2.16 g, 13 mmole 3-N,N-diethylaminophenol in 90 ml of n-butanol:toluene (2:1). The mixture was refluxed overnight with azeotropic removal of water. Progress of the reaction was followed by thin layer chromatography (TLC) using methanol:toluene (1:9). Next, the reaction mixture was distilled to remove about 40 ml toluene, followed by cooling of the reaction mixture to room temperature. Crystalline product was separated and dried at room temperature to give 2.5 g of product. UV (DMF) $\lambda$max 650 nm, $\epsilon=240,000$, fluorescence (DMF).

EXAMPLE 2

Preparation of
1-[4-[N-ethyl-N-(3-sulfopropyl)amino]-2-hydroxyphenyl]-3-[4-diheptylamino-2-hydroxyphenyl]-2,4-dihydroxycyclobutenediylium dihydroxide, bis(inner salt) (C₇ SAS)

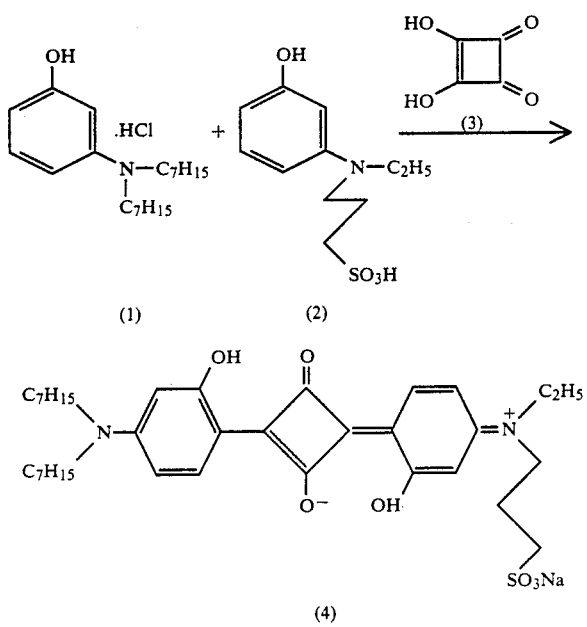

Preparation of Starting Materials

3-[N-ethyl-N-(3-hydroxyphenyl)amino]propane sulfonic acid was prepared as follows:

Propane sultone (1.22 g, 10 mmol) and 3-(ethylamino)phenol (1.37 g, 10 mmol) were warmed together in a 25 ml round bottom flask until melting began. After 5-10 minutes, 2 ml of methanol was added the liquified mixture. After 30 minutes, additional methanol was added (5-10 ml) and the mixture was heated to reflux. The dark lower layer solidified into a pale pink powder.

The solid was washed on a glass frit with hot methanol. It was then taken up in methanol at reflux and allowed to cool and crystallize. Dissolution in boiling methanol occured slowly with the slow formation of crystals. The resultant solid (2.04 g, 78%) was a single spot on TLC (silica, CH₃CN/H₂O 88:12 v/v; UV detection: R$_f$ 0.59).

m-(N,N-diheptylamino)phenol hydrochloride was prepared as follows:

A mixture of 3-aminophenol (3 g, 0.034 mole, Aldrich Chemical Co., Inc.), 1-iodoheptane (15.6 g, 0.069 mole, Aldrich Chemical Co. Inc.) and N,N-diisopropylethylamine (13.4 g, 0.104 mole, Aldrich Chemical Co., Inc.) in methanol (17 ml) was refluxed under nitrogen for 28 hours. The reaction product (R$_f$ 0.55, silica, ethylacetate:hexane 1:4 v/v) was then allowed to cool at room temperature and the solids of N,N-diisopropylethylamine hydroiodide were filtered off. To the resulting filtrate was added ether (500 ml) and the solids were again filtered off. The filtrate thus obtained was then evaporated to dryness to yield a red oil to which was then added 1N HCl (approx. 121 ml). The resulting bilayer liquid was then extracted using 100 ml ether. The ether layer was allowed to stand at room temperature for 30 minutes resulting in a crystalline product.

The crude crystalline product was recrystallized in 165 ml methanol:ether (1:10 v/v) to yield pure m-(N,N-diheptyl)aminophenol hydrochloride (6.0 g). Similarly, the crude product (2.0 g) from the mother liquor was recrystallized from methanol:ether to yield 1.2 g of pure m-(N,N-diheptyl)aminophenol hydrochloride. The total yield of product was 7.2 g (69%, mp 110°–111°).

A. Synthesis

A 100 ml, three-neck flask was fitted with a Dean-Stark trap condenser, and maintained under positive argon pressure. The solid 3-[N-ethyl-N-(3-hydroxyphenyl)amino]propane sulfonic acid, (906.5 mg, 3.5 mmole) was added to the flask followed by 20 ml of an azeotropically dried mixture of ethylene glycol and n-butanol (1:1). The mixture was heated in an oil bath until a clear solution was obtained.

The m-(N,N-diheptyl)aminophenol hydrochloride (1 g, 3.2 mole) was dissolved in 10 ml of an azeotropically dried mixture of n-butanol and benzene (1:2). Sodium bicarbonate (600 mg, 7 mmole) was slurried in the mixture and transferred to the reaction vessel by Pasteur pipet. Vigorous bubbling from the evolution of carbon dioxide quickly subsided. The mixture was refluxed for 30 minutes to remove any traces of water.

Reflux was halted, and squaric acid (400 mg, 3.5 mmole), was added all at once to the still hot mixture followed by an additional 5 ml of ethylene glycol-n-butanol mixture. The reaction mixture was again brought to reflux and blue color appeared within minutes. The reflux was maintained for approximately 7 hours at which time benzene was distilled off and the reaction was allowed to cool. The reaction vessel was stoppered and placed in the freezer for more than 48 hours.

The cold mixture was filtered to collect a quantity of dark, greenish-black crystals which were washed with cold n-butanol followed by methanol and then vacuum dried at 65° C. The recovered dye mixture weighed 1.3 g.

B. Purification

The detergent dye mixture was transferred to an extraction thimble in a Soxhlet apparatus. Extraction with a mixture of methanol-methylene chloride removed the 1,3-bis[4-(diheptylamino)-2-hydroxyphenyl]-2,4-dihydroxycyclobutenediylium dihydroxide, bis (inner salt), (THpS) and a small amount of C₇SAS dye. Methylene chloride was removed by evaporation using a Rotovap, and the THpS which crystallized from the residual methanol was removed by filtration. The methanol filtrate was diluted with additional methanol (approximately 250 ml total volume) and used to continue the extraction. When the extraction was complete, the flask was removed from the Soxhlet apparatus and the contents allowed to cool. Twenty-five grams (25 g) of RP-8 silica gel were added with stirring followed by the dropwise addition of 150 ml of water. Stirring was stopped and the supernatant decanted. The dark blue silica gel slurry was transferred to a column containing an additional 10 g RP-8 silica gel equilibrated with 40% water in methanol. The column was washed with 40% water in methanol until all 1,3-bis[4-[N-ethyl-N-(3-sulfopropyl)-amino]-2-hydroxyphenyl]2,4-dihydroxycyclobutenediylium dihydroxide, bis (inner salt) (BSAS) had been removed. The column was then washed with 30% water in methanol until C₇SAS began to elute. Elution was completed with 20% water in methanol. The fractions containing the C₇SAS dye were combined and stripped to dryness on the Rotovap and the residue dissolved in methanol-methylene chloride (1:1). The methylene chloride was slowly distilled off and the methanol was concentrated. After cooling, the dark-blue mixture was placed in the freezer at 0° C. overnight. Filtration and vacuum drying afforded 0.513 g of analytically pure C₇SAS as a greenish-black solid. The yield was 44% of theoretical.

Elemental analysis gave C=61.73, H=7.54, N=4.06, Na 3.23, which is consistent with the monohydrate of the sodium salt: SO₆N₂C₃₅H₄₇Na·H₂O.UV, $\lambda_{max}=642$ nm (MeOH).

EXAMPLE 3

Preparation of C₇SAS Using Dimethyl sulfoxide (DMSO)

A. Synthesis

A mixture of m-(N,N-diheptyl)aminophenol hydrochloride (1) (770 mg, 2.25 mmoles), 3-[N-ethyl-N-(3-hydroxyphenyl)amino]propane sulfonic acid (2) (678 mg, 2.5 mmoles), dihydroxy-3-cyclobutene-1,2-dione (3) (285 mg, 2.5 mmoles, Aldrich Chemical Co., Inc.), DMSO (4 ml) and sodium bicarbonate (389 mg) in 40 ml of n-butanol-benzene (2:1 by volume, predried for 2 hours using azeotrope) was refluxed under nitrogen with azeotropic removal of water for two hours. The mixture was allowed to stand at room temperature under nitrogen overnight. To the product was added ether (500 ml), and the resulting precipitates were filtered and washed with 50 ml of water. A crude preparation (370 mg) of the C₇SAS detergent dye (4) was obtained.

B. Purification

The purification of the C₇SAS detergent dye was as described in Example 2. The properties of the C₇SAS dye, i.e., the C₇SAS dye shows minimal leaching and can stain cells in the presence of plasma, make it a suitable replacement for the DEAS dye used in the blood typing assays as described in Examples 5, 6 and 7 as well as in antibody screening assays and cross-match.

EXAMPLE 4

Preparation of 1-[4-[N-ethyl-N-(3-sulfopropyl)amino]-2-hydroxyphenyl]-3-[4-dioctylamino-2-hydroxyphenyl]-2,4-dihydroxycyclobutenediylium dihydroxide, bis (inner salt) (C₈SAS)

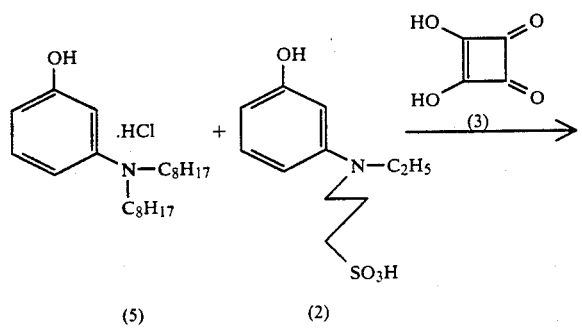

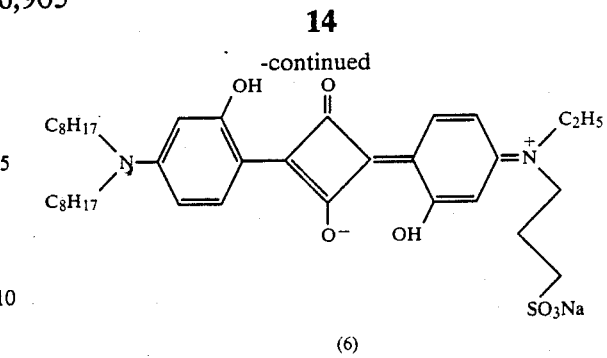

(6)

Preparation of starting materials:

m-(N,N-dioctyl)aminophenol hydrochloride, was prepared as follows:

A mixture of 3-aminophenol (5 g, 0.046 mole, Aldrich Chemical Co., Inc.), 1-iodooctane (22 g, 0.092 moles, Aldrich Chemical Co., Inc.) and N,N-diisopropylethylamine (18 g, 0.139 mole, Aldrich Chemical Co., Inc.) in methanol (25 ml) was refluxed under nitrogen for 24 hours. An aliquot of the reaction product was spotted on TLC (silica, 20% EtOAc:hexane). The TLC showed formation of dialkylated and monoalkylated product, therefore, additional amounts of iodooctane (10 g, 0.042 mole) were added and the resulting mixture was refluxed for an additional 4 hours.

The reaction product (R$_f$0.64, silica, 20% ethyl acetate:hexane was concentrated until a precipitate was formed. The resulting solids of N,N-diisopropylethylamine hydroiodide were collected and washed with ether. The filtration procedure was repeated one more time and the remaining filtrate was acidified using 1N HCl and extracted with ether. The ether layer was allowed to stand at room temperature until crystals formed. The crystals were collected to yield 560 mg of m-(N,N-dioctyl)aminophenol hydrochloride. The product was further purified on preparative TLC (silica, 2:1 ethyl acetate/hexane) with recovery of product by elution with 20% MeOH/CH₂Cl₂ resulting in a pure product (400 mg, mp 112°–114°). For the purification of larger quantities of material, recrystallization from methanol-ether is preferred.

The preparation of 3-[N-ethyl-N-(3-hydroxyphenyl)amino]propane sulfonic acid was as described in Example 2.

A. Synthesis

A mixture of m-(N,N-dioctyl)aminophenol hydrochloride (5) (600 mg, 1.62 mmoles), 3-[N-ethyl-N-(3-hydroxyphenyl)amino]propane sulfonic acid (2) (648 mg, 2.5 mmoles), squaric acid (3) (285 mg, 2.5 mmoles, from Aldrich Chemical Co., Inc.), DMSO (4 ml), and sodium bicarbonate (410 mg) in 40 ml of n-butanol-benzene (2:1 by volume, predried for 2 hours using azeotrope) was refluxed using azeotrope under nitrogen for two hours. It was then allowed to stand at room temperature under nitrogen overnight. The resulting blue dye was filtered and the precipitate washed with 5 ml of 0.1N HCl followed by 1 ml of water to yield crude C₈SAS squaraine dye (6) (700 mg).

B. Purification

Method 1: The crude C₈SAS squaraine dye (50 mg) was stirred in a small amount of water (approximately 1 ml), and the resulting suspension was filtered and washed with water until there was complete removal of the di-SO₃ squarate dye. The residual C₈SAS dye was then heated in methanol (approximately 10 ml) and filtered. To the resulting hot filtrate was then added 10 ml of ether and the mixture was cooled to 5° C. This method gave a yield of 7.8 mg of pure $C_8$ detergent dye. UV (DMSO,H+), $\lambda_{max}$=657.8 nm.

Method 2: The crude $C_8SAS$ detergent dye (120 mg) was dissolved in approximately 5 ml of 20% MeOH/$CH_2Cl_2$ and chromatographed on eight thick layer silica gel plates (Analtech Uniplate, silica gel GF, 20×20 cm, 1000 microns, Catalog No. 02013). The band in the center (Rf 0.48) was scraped off and eluted, using 30% MeOH/$CH_2Cl_2$ to yield 15 mg of purified $C_8$-SAS detergent dye.

EXAMPLE 5

Assay for the Determination of the D (Rho) Blood Group Antigen

A saturated solution of DEAS in dimethylformamide (DMF) was prepared and then diluted 1:10 (by volume) with DMF. Fifty μl of the diluted DEAS solution was mixed dropwise with 1 ml of a whole blood sample. Immediately thereafter, ten μl of this mixture was mixed with 10 μl of antibody (commercially available typing reagent) specific for the D ($Rh_o$) blood group antigen. The mixture was held for one minute at ambient temperature and then diluted with 1.5 ml of phosphate buffer containing serum albumin and sucrose.

The medium was analyzed for a change in fluorescence as a result of agglutination of cells by means of the limited volume method and apparatus for particle counting disclosed in U.S. Pat. No. 4,564,598 issued Jan. 14, 1986.

The single fiber end of a "Y"-shaped fiber optics coupler obtained from Kaptron, Inc., Palo Alto, Calif. (Splitter-Monitor, Model FOMS-850-P), was submerged in the medium. The fiber had a diameter of 50 microns and produced an excitation cone with a half angle of 12° and an effective sampling volume of $1 \times 10^{-7}$ ml. Excitation light from a He-Ne laser (632.9 nm) was fed into one of the two branch fibers. The portion of the fluorescence emitted from the cells which entered the submerged fiber end was split at the fiber juncture to transmit equal halves back along the two branch fibers. The portion traveling through the second branch fiber was then read on a high-gain EMI photomultiplier after filtering out interference within gate times of one millisecond at the rate of one every 0.1 second for periods of time ranging from 50 to 500 seconds. The average number of fluorescent pulses per gate time was then determined by computer. To obtain the mean fluorescence (x), variations in the fluorescent pulses per gate time were quantified by fluctuations or peak height analysis.

Two types of control runs were made to establish a standard emission level.

(a) Samples that were typed as D ($Rh_o$) negative by conventional typing were assayed in the same way.

(b) A commercially available "Rh control" reagent which includes all the ingredients of a D ($Rh_0$) typing reagent except for the antibody was used in the above assay in place of the antibody reagent.

The results from samples from five positive and five negative individuals are summarized in Table 1.

TABLE 1

| Type | Signal* |
|---|---|
| D ($Rh_o$) positive | 84 |
| | 108 |
| | 72 |
| | 46 |
| D ($Rh_o$) neqative | 74 |
| | 18 |
| | 23 |
| | 22 |
| | 17 |
| Control | 20 |
| | 21 |
| | 19 |
| | 17 |

*Signal was obtained by fluctuation analysis as described in the specification, Signals greater than 40 were regarded as positive.

EXAMPLE 6

Assay for the Determination of the Antibody Specific for the A Blood Group Antigen Whole type A blood was centrifuged at 2800 rpm and the supernatant and buffy coat of the white cells were removed by aspiration. The packed cells were washed free of plasma using isotonic buffered saline and suspended at 50% hematocrit in buffer containing 10% bovine serum albumin.

A saturated solution of DEAS in DMF was prepared and diluted 1:10 (by volume) with DMF. Fifty μl of the diluted DEAS solution was mixed dropwise under continuous vortexing with 1 ml of the above type A cell suspension.

Ten μl of the above suspension was mixed with 20 μl of a whole blood sample. The mixture was held for one minute at ambient temperature diluted with 3 ml of buffer containing serum albumin and dextran, and analyzed as described above in Example 5 using the limited volume method and apparatus for particle counting. The results are summarized in Table 2.

TABLE 2

| Group* | Signal** |
|---|---|
| A | 18 |
| | 23 |
| | 25 |
| | 13 |
| | 18 |
| B | 112 |
| | 110 |
| | 91 |
| | 107 |
| | 56 |
| AB | 35 |
| | 25 |
| | 19 |
| | 22 |
| | 18 |
| O | 106 |
| | 134 |
| | 81 |
| | 116 |
| | 80 |
| Control*** | 15 |
| | 18 |
| | 16 |

*Samples from five separate individuals having the listed blood groups were tested.
**Signal was obtained by fluctuation analysis as described in specification, Signals greater than 40 were regarded as positive.
***Control signals were obtained by reacting the A cells with blood from individuals who were known to be of AB type.

EXAMPLE 7

The assay of Example 5 was repeated for blood group antigens A, B, and O using antibody specific for the A(α A) and B(α B) blood group antigens and antibodies obtained from type O individuals (α A,B), respectively. The results are summarized in Table 3.

TABLE 3

| Blood Type | Reagent | Signal* |
|---|---|---|
| A | αA | 103 |
|   | αB | 21 |
|   | αA,B | 74 |
|   | Control - no reagent | 21 |
| B | αA | 19 |
|   | αB | 100 |
|   | αA,B | 113 |
|   | Control - no reagent | 22 |
| O | αA | 18 |
|   | αB | 22 |
|   | αA,B | 17 |
|   | Control - no reagent | 23 |

*Signal was obtained by fluctuation analysis as described in the specification. Signals greater than 40 were regarded as positive.

EXAMPLE 8

Staining of Reagent Red Blood Cells

A. $C_7SAS$ Detergent Dye in saline

Human erythrocytes were washed in isotonic saline and suspended to approximately $4 \times 10^9$ cells/ml in saline containing 20 g/l bovine serum albumin (BSA).

Squaraine sulfonate dye, $C_7SAS$, (100 ul, $10^{-4}$M in dimethylacetamide) was added dropwise to 1 ml of saline containing BSA with continuous vortexing. The solution was immediately added to 1 ml of the cell suspension, dropwise with continous vortexing. The resulting cell suspension was then mixed gently. The cells were washed in isotonic saline and stored at approximately $5 \times 10^8$ cells/ml (5% hematocrit) for reverse grouping and $1 \times 10^9$ cells/ml (10% hematocrit) for antibody screening, in an isotonic cell storage medium.

Fluorescence was determined by diluting 10 ul of 10% hematocrit cells in 0.5 ml saline and measuring the mean fluorescence ($\bar{x}$) as described in Example 5. Incorporation of fluorescence into cells over time is illustrated in Table 4.

TABLE 4

| Time (min.) | $\bar{x}$ |
|---|---|
| 1 | 4 |
| 30 | 100 |
| 60 | 138 |
| 90 | 160 |
| 120 | 176 |
| 150 | 168 |

An $\bar{x}$ value of approximately 100 was found to provide sufficient instrument sensitivity and could be achieved within approximately 30 minutes of mixing the cells with the dye in saline/BSA.

B. $C_7SAS$ in plasma 50 ul of $C_7SAS$ detergent dye ($1 \times 10^{-4}$M in dimethylacetamide) was mixed with 1 ml of whole blood. At the time intervals shown in Table 5, a portion of the sample was centrifuged. The cells were washed and resuspended in saline prior to fluorescence measurements. Table 5 shows the fluoresence ($\bar{x}$) of the cells over time.

TABLE 5

| Time (min.) | Fluorescence ($\bar{x}$) |
|---|---|
| 0 | 43 |
| 11 | 55 |
| 60 | 110 |
| 180 | 176 |

TABLE 5-continued

| Time (min.) | Fluorescence ($\bar{x}$) |
|---|---|
| 300 | 229 |

C. $C_8SAS$ in saline

Red cells were washed in saline and suspended to 20% hematocrit in suspension medium (2% BSA, 2% pluronic or 0.4% β-cyclodextrin). To 1 ml of the cell suspension was added with vortexing 50 μl of $1 \times 10^{-4}$M $C_8SAS$ dye solution in dimethylacetamide. The cells were allowed to stand at room temperature for 10 minutes and were then washed in saline and suspended in an isotonic cell storage medium. The resulting fluorescence in three different suspension media is shown in Table 6.

TABLE 6

| Suspension media | Fluorescence ($\bar{x}$) |
|---|---|
| 2% BSA | 41 |
| 2% Pluronic | 106 |
| 4% β-cyclodextrin | 109 |

EXAMPLE 9

Loss of Dyes from Stained Cells During Assay Incubation

To measure the loss of fluorescence from stained cells during incubation with sample at 37° C., the cells were stained with various squaraine dyes and suspended to 0.9% by volume in a 1:1 (vol:vol) mixture of plasma in a low ionic strength solution (LISS). The mixtures were incubated in test tubes at 37° C. At selected time intervals, the test tubes were removed, the cells separated by centrifugation, washed in saline and resuspended in 0.5 ml saline. The fluorescence of the suspensions ($\bar{x}$) was measured as described in Example 8. Table 7 shows the relative fluorescence of the cells when stained with the various dyes.

TABLE 7

| | Fluorescene ($\bar{x}$) | | |
|---|---|---|---|
| Time (min) | DEAS | $C_7SAS$ | $C_8SAS$ |
| 0 | 100 | 100 | 100 |
| 5 | 5 | 104 | 102 |
| 10 | 6 | 102 | 102 |
| 15 | 7 | 98 | 99 |

Table 7 shows the relatively slow rate of leaching of the detergent dyes, $C_7SAS$ and $C_8SAS$ compared to DEAS under actual antibody screen and cross-match assay conditions. DEAS stains cells very rapidly, as shown in Example 5, compared to the rate of staining of cells when $C_7SAS$ is used (Example 8) and is therefore preferred in assays that do not require substantial dilution or separation of the stained cells.

EXAMPLE 10

Use of $C_7SAS$ Stained Cells in Reverse Grouping

10 μl (5% hematocrit) of cells stained with $C_7SAS$ dye was placed in a reaction cup and 50 μl of the blood sample added. After mixing for 2 minutes, the suspension was diluted with 0.5 ml saline and a measurement taken to determine the agglutination index. The results are shown in Table 8.

TABLE 8

Agglutination Indices resulting from mixing cells stained with C₇SAS with blood samples having various AB0 Types:

| | Blood Type | | |
|---|---|---|---|
| | B | A | AB |
| Type B Cells | 21 | 921 | 60 |
| | 66 | 11752 | 15 |
| | 69 | 9138 | 98 |
| | 37 | 13336 | 83 |
| | 64 | 10750 | 34 |
| | 59 | 4066 | |
| Type A Cells | 19494 | 121 | ND |
| | 17266 | 85 | ND |
| | 14666 | 72 | ND |
| | 19921 | | ND |

Table 8 shows that standard B cells are agglutinated with blood that does not have the B antigen and therefore, has anti-B-antibodies. Stained A cells are agglutinated with blood that does not have the A antigen and therefore, has anti-A-antibodies. The use of the DEAS dye is not effective in this particular type of assay due to the leaching out of the dye and resulting loss of signal.

EXAMPLE 11

Use of C₇SAS Stained Cells for Antibody Screen Assays

For each sample, 10 μl of 10% hematocrit screen cells stained with C₇SAS dye by the methods previously described was incubated with 50 μl of either fresh or previously frozen plasma and 50 μl of LISS, for 10 minutes at 37° C. in a glass test tube. The samples were washed with LISS by centrifugation or magnetic separation. The resulting cell suspension was diluted to 40 μl with LISS and applied to a latex reaction block with 10 μl of anti-human globulin-PVP reagent. An automated protocol was used which mixed the reactants then diluted the sample and measured the agglutination index. Table 9 shows representative agglutination indices (AI) values for positive and negative samples.

TABLE 9

| Antibody | | AI |
|---|---|---|
| Anti-E | positive | 15200 |

TABLE 9-continued

| Antibody | | AI |
|---|---|---|
| | negative | 220 |
| Anti-Fy[a] | positive | 1302 |
| | negative | 115 |
| Anti-Jk[a] | positive | 804 |
| | negative | 166 |

The above data demonstrate that the method of the invention has utility for assaying for a wide variety of analytes and has particular utility in blood typing. The method is simple and rapid.

Although the foregoing invention has been described in some detail by way of illustration and example for purposes of clarity and understanding, it will be obvious that certain changes or modifications may be practiced within the scope of the appended claims.

What is claimed is:

1. A compound of the formula:

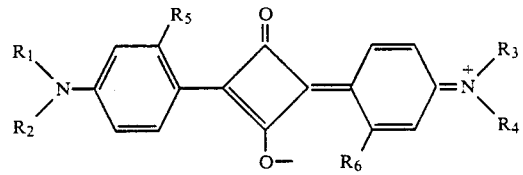

wherein:
$R_1$ and $R_2$ are independently selected from the group consisting of lower alkyl (1–5 carbon atoms) with the proviso that at least one of the $R_1$ and $R_2$ groups has a substituent selected from the group consisting of $-SO_3H$, $-OSO_3H$, $-PO_3H_2$, $-OPO_3H_2$, $-COOH$ and $-NHSO_3H$;

$R_3$ and $R_4$ are independently selected from the group consisting of alkyl (5–15 carbon atoms); and $R_5$ and $R_6$ are independently selected from the group consisting of hydrogen, hydroxyl, and lower alkoxyl (1–5 carbon atoms).

2. The compound of claim 1 wherein the substituent of $R_1$ and $R_2$ is $-SO_3H$.

3. The compound of claim 1 wherein $R_1$ is lower alkyl (1–5 carbon atoms); $R_3$ and $R_4$ are alkyl (5–15 carbon atoms); and $R_2$ is $-(CH_2)_nSO_3H$, where n is 2–5.

4. The compound of claim 3 wherein $R_1$ is ethyl, $R_3$ and $R_4$ are heptyl and n is 3.

* * * * *